United States Patent [19]

Choudhary et al.

[11] Patent Number: 5,336,825
[45] Date of Patent: Aug. 9, 1994

[54] INTEGRATED TWO STEP PROCESS FOR CONVERSION OF METHANE TO LIQUID HYDROCARBONS OF GASOLINE RANGE

[75] Inventors: Vasant R. Choudhary; Subhash D. Sansare; Sopan T. Chaudhari, all of Maharashtra, India

[73] Assignee: Council of Scientific & Industrial Research, New Delhi, India

[21] Appl. No.: 912,969

[22] Filed: Jul. 10, 1992

[51] Int. Cl.$^5$ .............................................. C07C 2/00
[52] U.S. Cl. ................................... 585/500; 585/654; 585/658; 585/656; 585/943
[58] Field of Search ............... 585/500, 654, 656, 658, 585/943

[56] References Cited

U.S. PATENT DOCUMENTS

| | | | |
|---|---|---|---|
| 4,567,307 | 1/1986 | Jones et al. | 585/943 |
| 4,704,487 | 11/1987 | Devries et al. | 585/943 |
| 4,801,762 | 1/1989 | Leyshon | 585/943 |
| 4,814,538 | 3/1989 | Devries et al. | 585/943 |

*Primary Examiner*—Helen M. S. Sneed
*Assistant Examiner*—E. D. Irzinski
*Attorney, Agent, or Firm*—Abelman Frayne & Schwab

[57] ABSTRACT

This invention discloses an improved integrated two step process for conversion of methane to liquid hydrocarbons of gasoline range. The invention particularly comprises catalytic oxidative conversion of methane with free oxygen to ethylene and higher olefins containing gaseous product in the first step and catalytic conversion of the olefins from the product stream of the first step without separating them to liquid hydrocarbons of gasoline range in the second step, for the conversion of methane to liquid hydrocarbons. The process of the present invention could be used in the petroleum industry for the production of gasoline and liquid hydrocarbon fuels and aromatic hydrocarbons.

15 Claims, No Drawings

INTEGRATED TWO STEP PROCESS FOR CONVERSION OF METHANE TO LIQUID HYDROCARBONS OF GASOLINE RANGE

This invention relates to an improved integrated two-step process for conversion of methane to liquid hydrocarbons. This invention particularly relates to a novel two-step process comprising catalytic oxidative conversion of methane with free oxygen to ethylene and higher olefins (viz. propylene and butylenes) containing gaseous product in the first step and catalytic conversion of the olefins from the product stream of the first step without separating them to liquid hydrocarbons of gasoline range in the second step, for the conversion of methane to liquid hydrocarbons. The process of the present invention could be used in petroleum industry for the production of gasoline and liquid hydrocarbon fuels, and aromatic hydrocarbons.

Methane is a major constituent of natural gas and also of biogas. Methane is used principally as a source of heat in commercial, industrial and residential services and also a source of hydrogen for fertilizer industries and syngas (CO and $H_2$) for the production of methanol and in Fischer-Tropsch synthesis. World reserves of natural gas of which methane is a main constituent are constantly being upgraded and more natural gas being discovered than oil. Because of the problems associated with transportation of a very large volumes of natural gas, most of the natural gas produced, particularly at remote places, is flared and hence wasted. If efficient technology were available for the conversion of methane to easily transportable and value added products such as liquid hydrocarbons, this can have a far reaching economic impact and also lead to exploration of more gas-rich fields increasing the natural gas reserves.

Earlier processes for conversion of methane to liquid hydrocarbons are based on the conversion of methane to syngas, methanol, methylchloride or ethylene in an intermediate stage.

Processes Based on Conversion of Methane to Syngas and Methanol

Earlier conventional processes for conversion of methane/natural gas in to liquid hydrocarbons are based on the conversion of syngas (a mixture of carbon monoxide and hydrogen), obtained from methane/natural gas, to aliphatic hydrocarbons by a well known Fischer-Tropsch synthesis and to methanol which is further converted to liquid hydrocarbons by Mobil's MTG processes [P. W. Alpin, Chem. Eng. Aust. 7-13, (1986), C. J. Maiden, Chemtech, 18(1), 38, 42, (1988)].

The conversion of methane to liquid hydrocarbons by both the Fischer-Tropsch and methanol routes are more-or-less established technology. Both the Fischer-Tropsch route and the methanol routes from methane to higher hydrocarbons requires the primary conversion of methane to synthesis gas as the first step, then the syngas is converted in the second step to aliphatic hydrocarbons in the Fischer-Tropsch synthesis or to methanol which is further converted in the next step to liquid hydrocarbons in the MTG process. These processes suffer from the requirement of complicated engineering steps and also from the relative inefficiency of carrying out extensive oxidation of methane to carbon monoxide and then reduction of carbon monoxide to aliphatic hydrocarbons in the Fischer-Tropsch synthesis or to methanol in the MTG process.

Conversion of Methane to Gasoline Range Hydrocarbons via Methyl Chloride

Recently, Taylor et al. has described a two stage process for producing gasoline range hydrocarbons from methane via methyl chloride (Taylor et al. Procd. 9th Intl. Congr. Catal., Vol. 2, p. 990, 1988; Stud. Surf. Sci. Catal., Vol. 36, p. 483, 1988). In the first step methane is catalytically oxyhydrochlorinated selectively to methyl chloride and the resulting methyl chloride is converted in the second stage to gasoline range hydrocarbons over ZS M-5 catalyst. This process suffers from a number of disadvantages such as requirement of HCl in large or stoichiometric amounts in the formation of methyl chloride from methane, formation of unwanted polychloromethanes conversion of which to higher hydrocarbons requires addition of hydrogen and also the corrossion problems due to the presence of HCl, $H_2O$ and chloromethanes. Therefore this process is not commercially feasible.

Higher Hydrocarbons from Methane via Ethylene

According to U.S. Pat. No. 4,567,307 (1986), methane containing gas is converted to hydrocarbons having a greater carbon number than 1 in a two stage process consisting of contacting methane with one or more reducible metal oxides (Oxides of Mn, Sn, In, Ge, Sb, Bi and Pb) at 500°–1000° C., separating hydrocarbons having a greater carbon number than 1 from water and converting the product to higher hydrocarbons over an oligomerization catalyst. The main drawback of this process is the use of reducible metal oxides for the conversion of methane to ethylene in the first stage; because reduced metal oxides are to be reoxidized and hence redox operation is essential. The redox operation is very complicated. It requires a complicated reactor consisting of physically separate zones for a methane contacting step and for an oxygen contacting step with an arrangement for recirculating the metal oxides between the two zones. Further, because of the redox operation and the requirement of lower space velocity of methane to achieve reasonable methane conversion, the productivity of ethylene is low.

In U.K. Patent Appl. G.B.2,191,212 (1987), an integrated process for the manufacture of liquid hydrocarbons from methane has been described. The process consists of (i) feeding methane to pyrolysis zone to form a product comprising $H_2$, unsaturated hydrocarbons and aromatic hydrocarbons, (ii) reacting the pyrolysis product in an oligomerization/alkylation zone, (iii) reacting the oligomerization/alkylation product with part of $H_2$ remaining in the product thereby hydrogenating the unsaturated hydrocarbons in the oligomerization-/alkylation product and (iv) recovering the liquid hydrocarbon from product stream. This process suffers from the disadvantage that the pyrolysis of methane is a highly endothermic process and also involve coking reactions leading to formation of coke.

The main object of the present invention is to provide a novel integrated two-step process, which is commercially viable and energy-efficient, for the production of gasoline range hydrocarbons from methane by carrying out catalytic oxidative conversion of methane to ethylene and lower olefins in presence of free oxygen in the first step and catalytic conversion of the olefins formed in the first step, without separating them from the product stream, to liquid hydrocarbons of gasoline range in the second step, using the product stream of the first step as a feed.

The main finding of the present invention is that methane can be converted to gasoline range hydrocarbons (i.e. $C_5$ to $C_{10}$ hydrocarbons) with high yields in an energy-efficient manner by carrying out the conversion of methane in the following two integrated steps:

Step-I: Catalytic oxidative conversion of methane to ethylene and minor amounts of $C_2$ and $C_4$ olefins in presence of free oxygen using basic solid catalysts.

Step-II: Catalytic conversion of the ethylene and higher olefins formed in the Step-I to liquid hydrocarbons of gasoline range over acidic solid catalyst containing high silica pentasil zeolite, using product stream of the Step-I as a feed.

Accordingly, the present invention provides an improved integrated two-step process for the conversion of natural gas to liquid hydrocarbons of gasoline range which comprises passing a gaseous reactant mixture comprising methane and oxygen (or air) with or without steam over basic solid catalyst suitable for oxidative coupling of methane to $C_2$-hydrocarbons in presence of free oxygen in a fixed bed reactor to produce gaseous products comprising ethylene, ethane, $C_{3+}$ olefins, $C_{3+}$ paraffins, carbon oxides and water vapours and if required, separating the water vapours from the product stream by condensation. The basic solid catalyst is chosen from the known catalysts (viz. rare earth metal-promoted alkaline earth metal oxides, PbO-promoted MgO, Li-promoted MgO and like) used in oxidative coupling of methane to $C_2$-hydrocarbons in presence of free oxygen.

The process operating conditions for the first step are as follows.

| | |
|---|---|
| Pressure | 1–50 atm (preferably 1–2 atm) |
| Reaction temperature | 500°–1000° C. (preferably 600°–850° C.) |
| Gas hourly space velocity (GHSV) | 500–5,000,000 $h^{-1}$ (preferably 2000–2,000,000 $h^{-1}$) |
| Concentration of $CH_4$ in feed | 1 to 99% (preferably 20 to 95 mol %) |
| Concentration of $O_2$ in feed | 0.1 to 40 mol % (preferably 1 to 35 mol %) |
| $CH_4/O_2$ ratio in feed | 1.5 to 100 (preferably 2–20) |
| Concentration of $N_2$ or Ar or their mixture in feed | 0 to 80 mol % |
| Concentration of water vapour in feed | 0 to 90 mol % |
| Concentration of $CO_2$ in feed | 0 to 30 mol % |
| Concentration of CO in feed | 0 to 5 mol % |
| Concentration of $C_2H_6$ in feed | 0 to 5 mol % |

In the first step of the said integrated process, the products formed are ethylene, ethane, water and oxides of carbon (i.e. CO and $CO_2$) as major products, $C_3$–$C_4$ olefins and $C_3$–$C_4$ paraffins as minor products, and $C_{5+}$ hydrocarbons only in traces. The gaseous product stream obtained from the first step comprises of the above mentioned products, unconverted reactants (i.e. methane and oxygen) and components of feed other than the reactants.

The second step of the said two-step process comprises passing continuously the product stream of the first step of the said two-step process over a known solid acid catalyst containing high silica pentasil zeolite like H-ZSM-5, H-ZSM-8, H-ZSM-11, Pt-H-ZSM-5.Al-$_2O_3$ and the like having channel diameter of 5–6 Å in a fixed bed reactor at a pressure in the range of 1–50 atmospheres, temperature in the range of 200°–700° C. and a gas hourly space velocity in the range of 100–50,000 $h^{-1}$, separating the liquid hydrocarbons, $C_3$–$C_4$ hydrocarbons (or liquified petroleum gas i.e. LPG) and oxides of carbon by known manners and, if required, recycling the $C_1$–$C_2$ hydrocarbons and oxygen in the product stream to the first step.

For the second step of the said two-step process, the preferred pressure range may be 2 to 30 atmospheres, the preferred temperature range may be 300° to 600° C. and preferred gas hourly space velocity range may be 200 to 20,000 $h^{-1}$.

The products formed in the second step of the said two-step process of the invention are liquid hydrocarbons of gasoline range (i.e. $C_5$–$C_{10}$ hydrocarbons), $C_3$–$C_4$ hydrocarbons (or LPG) and small amounts of methane and ethane.

The present invention reveals that methane gas can be converted to liquid hydrocarbons of gasoline range in high yields by the said two-step process described above.

In the first step of the said two-step process of the invention, the conversion of methane as high as 18–40% with 60–80% selectivity for $C_{2+}$ hydrocarbons in the oxidative coupling of methane giving 2.5–7.5 mol % ethylene in the product stream, after removal of water by condensation, could be achieved.

In the second step of the said two-step process of the invention, ethylene at concentration as low as 2.5–7.5 mol % in the feed stream could be converted almost completely in the presence of CO, $CO_2$, $O_2$ and $CH_4$, giving yield for liquid hydrocarbons of gasoline-range as high as 70% or above.

The present invention is described with respect to the following examples. These are provided for illustrative purpose only and are not to be construed as limitation on the invention.

Definitions of Terms Used in the Examples

Conversion of methane in the first step of the said process is given in terms of percentage of methane in the feed converted to carbon containing products viz, ethylene, ethane, $C_{3+}$ hydrocarbons, CO and $CO_2$.

Selectivity for a particular product in the first step of the said process is obtained from the conversion of methane to a particular product and the total conversion of methane to carbon containing products, as follows.

Selectivity (%) =

$$\left( \frac{\text{Conversion of methane to a particular product}}{\text{Total conversion of methane (\%)}} \right) \times 100$$

Yield for a particular product in the first step of the said process is obtained as follows.

Yield (%) = [Total conversion of methane (%) × Selectivity (%) for a particular product] ÷ 100

Gas Hourly Space Velocity (GHSV) is the volume of feed gases (measured at STP) passed through a unit volume of catalyst per hour.

Conversion of ethylene in the second step of the said process is obtained as follows.

Conversion of ethylene (%) = {[Ethylene in hydrocarbon feed (wt %) − ethylene in hydrocarbon products (wt %)] ÷ [Ethylene in hydrocarbon feed (wt %)]} × 100

Yield and selectivity for different products in the second step of the said process is obtained from the conversion of ethylene to a particular product and the total conversion of ethylene, as follows:

Yield (%) = Conversion of ethylene to a particular product (%)

Selectivity (%) =

$$\frac{\text{Conversion of ethylene to a particular product (\%)}}{\text{(Total conversion of ethylene (\%))}} \times 100$$

The product concentrations are expressed in mole %. Conversion given in the examples is per pass conversion.

EXAMPLE-1

Conversion of methane to liquid hydrocarbons has been carried out in the following integrated two steps.

Step-I: Catalytic Oxidative Conversion of Methane to Ethylene, Ethane and $C_{3+4}$ Hydrocarbons The catalytic methane conversion reaction was carried out by passing a mixture of reactants (viz. methane and $O_2$) with or without water vapours over a basic solid catalyst (22–30 mesh size) in a flow reactor (i.d.: 10 mm) made up of quartz. The reactor temperature was measured by Chromel-Alumel thermocouple located in the catalyst bed. The reactor effluent gases were cooled by water condenser, to remove water vapours from the product and then analysed for ethane, ethylene, higher hydrocarbons, CO, $CO_2$ and unconverted methane and oxygen by an on-line gas chromatograph using Porapak-Q and spherocarb columns. The catalyst used was La-promoted MgO ($La_2O_3$-MgO, with La/Mg ratio=0.1). It was prepared by impregnating magnesium carbonate with lanthanum nitrate and calcining in air at 950° C. for 2 hours.

The reaction was carried out at the following process conditions.

| Feed | A mixture of $CH_4$ and $O_2$ |
|---|---|
| $CH_4/O_2$ ratio in feed | 4.0 |
| GHSV | 51,000 h$^{-1}$ |
| Temperature | 850° C. |
| Pressure | 1.05 atm. |

The results obtained were as follows:

The total conversion of methane was 27.5% with a selectivity for ethane and ethylene of 64.9%.

The composition of the gaseous product stream, after removal of water vapours, was 5.0% ethylene, 4.6% ethane, 77.9% methane, 0.2% propylene and butanes, 0.1% propane and butanes, 8.6% $CO_2$, 1.6% CO, 2.0% $O_2$, etc.

Step-II: Catalytic Conversion of Ethylene and Other Olefins from the Product Stream of Step-I to Liquid Hydrocarbons The gaseous product stream of the Step-I was compressed and then passed over Pt.H-ZSM-5.$Al_2O_3$ (0.1 wt % Pt and 50 wt % $Al_2O_3$) catalyst in the form of 1/16″ extrudes packed in a fixed bed stainless steel reactor (internal diameter: 2 cm) at the following process conditions.

| Temperature | 500° C. |
|---|---|
| Pressure | 20.0 atm |
| Gas Hourly Space Velocity | 4800 h$^{-1}$ |
| (GHSV) | |

The reaction temperature was measured by a Chromel-Alumel thermocouple located in the centre of the catalyst bed. After 1 hour of start of the reaction analysis of the products was done using an on-line gas chromatograph. For this purpose the product stream, after reduction of the pressure, was passed through a heated gas sampling valve connected to the gas chromatograph. All the connecting lines to gas chromatographs were heated for avoiding the condensation of products in the lines. The product stream coming out from the gas sampling valve was cooled using a chilled water condenser and the condensed liquid products (i.e. liquid hydrocarbons) were collected. The gaseous products were measured by a gas meter and analysed by the gas chromatograph. The results obtained were as follows:

| Total conversion of ethylene | 94.2% |
|---|---|
| Selectivity for liquid hydrocarbons ($C_{5+}$ hydrocarbons) | 72.6% |
| Selectivity for $C_{3+4}$ hydrocarbons | 27.% |

EXAMPLE-2

Conversion of methane to liquid hydrocarbons in the two steps was carried out by the procedures described in EXAMPLE-1 at the following process conditions.

Step-I: Catalytic Oxidative Conversion of Methane to Ethylene, Ethane and $C_{3+4}$ Hydrocarbons.

The catalyst was same as that used in EXAMPLE-1.

| Process conditions employed in Step-I | |
|---|---|
| Feed | A mixture of $CH_4$ and $O_2$ |
| $CH_4/O_2$ ratio in feed | 6.0 |
| Space velocity | 51,000 (cm$^3 \cdot$ g$^{-1} \cdot$ h$^{-1}$) |
| Temperature | 852° C. |
| Pressure | 1.05 atm |

The results obtained were as follows. The total conversion of methane and the selectivity for ethylene and ethane were 22.4% and 74.1%, respectively. The composition of product stream after removal of water, was ethylene-4.2%, ethane-4.7%, methane-82.9%, propylene and butenes≅0.1%, propane and butanes≅0.1%, CO-0.6%, $CO_2$-5.4% and $O_2$-2.0%, etc.

Step-II: Catalytic Conversion of Ethylene and Other Olefins from the Product Stream of Step-I to Liquid Hydrocarbons

| Process conditions employed in Step-II | |
|---|---|
| Temperature | 400° C. |
| Pressure | 14.5 atm |
| GHSV | 1200 h$^{-1}$ |

The results obtained were as follows:

| Total conversion of ethylene | 97.7% |
|---|---|
| Selectivity for liquid hydrocarbons ($C_5$-$C_{10}$ hydrocarbons) | 55.9% |
| Selectivity for $C_3 + C_4$ hydrocarbons (LPG) | 36.1% |

EXAMPLE-3

Conversion of methane to liquid hydrocarbons in the two steps was carried out by the procedures described in EXAMPLE-1 at the following process conditions.

Step-I: Catalytic Oxidative Conversion of Methane to Ethylene, Ethane and $C_{3+4}$ Hydrocarbons The catalyst used was La-promoted CaO ($La_2O_3$-CaO with La/Ca=0.05). It was prepared by impregnating calcium hydroxide with lanthanum nitrate and calcining at 950° C. for 2 hours.

| Process conditions employed in Step-I | |
|---|---|
| Feed | A mixture of $CH_4$ and $O_2$ |
| $CH_4/O_2$ ratio in feed | 8.0 |
| Space velocity | 55,000 ($cm^3 \cdot g^{-1} \cdot h^{-1}$) |
| Temperature | 756° C. |
| Pressure | 1.2 atm |

The results obtained were as follows. The total conversion of methane and the selectivity for ethylene and ethane were 18.5% and 71.2%, respectively. The composition of product stream after removal of water was ethylene-2.7%, ethane-4.3%, methane-86.1%, propylene and butenes <0.1%, propane and butanes <0.1%, CO-1.3%, $CO_2$-4.1% and $O_2$-1.3%, etc.

Step-II: Catalytic Conversion of Ethylene and Other Olefins from the Product Stream of Step-I to Liquid Hydrocarbons

| Process conditions employed in Step-II | |
|---|---|
| Temperature | 490° C. |
| Pressure | 15.0 atm |
| GHSV | 2400 $h^{-1}$ |

The results obtained were as follows.

| | |
|---|---|
| Total conversion of ethylene | 87.1% |
| Selectivity for liquid hydrocarbons ($C_5$–$C_{10}$ hydrocarbons) | 46.8% |
| Selectivity for $C_3 + C_4$ hydrocarbons (LPG) | 45.6% |

EXAMPLE-4

Conversion of methane to liquid hydrocarbons in the two steps was carried out by the procedures described in EXAMPLE-1 at the following process conditions.

Step-I: Catalytic Oxidative Conversion of Methane to Ethylene, Ethane and $C_{3+4}$ Hydrocarbons The catalyst used was Sm-promoted MgO ($Sm_2O_3$-MgO) with Sm/Mg ratio=0.11). It was prepared by impregnating magnesium carbonate with samarium acetate and calcining in air at 950° C. for 10 hours.

| Process conditions employed in Step-I | |
|---|---|
| Feed | A mixture of $CH_4$ and $O_2$ |
| $CH_4/O_2$ ratio in feed | 4.0 |
| Space velocity | 51,300 $cm^3 \cdot g^{-1} \cdot h^{-1}$ |
| Temperature | 701° C. |
| Pressure | 1.1 atm |

The results obtained were as follows. The total conversion of methane and the selectivity for ethylene, ethane and $C_{3+4}$ hydrocarbons were 29.2% and 61.6%, respectively. The composition of product stream after removal of water, was ethylene-4.8%, ethane-4.1%, methane-76.1%, propylene and butenes-0.4%, propane and butanes <0.1%, .CO-2.6%, $CO_2$-9.0% and $O_2$-3.0%, etc.

Step-II: Catalytic Conversion of Ethylene and Other Olefins from the Product Stream of Step-I to Liquid Hydrocarbons

| Process conditions employed in Step-II | |
|---|---|
| Temperature | 510° C. |
| Pressure | 16.1 atm. |
| GHSV | 1200 $h^{-1}$ |

The results obtained were as follows.

| | |
|---|---|
| Total conversion of ethylene | 94.3% |
| Selectivity for liquid hydrocarbons ($C_5$–$C_{10}$ hydrocarbons) | 52.5% |
| Selectivity for $C_3 + C_4$ hydrocarbons (LPG) | 41.7% |

EXAMPLE-5

Conversion of methane to liquid hydrocarbons in the two steps was carried out by the procedures described in EXAMPLE-1 at the following process conditions.

Step-I: Catalytic Oxidative Conversion of Methane to Ethylene, Ethane and $C_{3+4}$ Hydrocarbons The catalyst used was Li-promoted MgO prepared by impregnating magnesium carbonate with $Li_2CO_3$ (Li/Mg=0.1) and calcining at 750° C. for 6 hours.

| Process conditions employed in Step-I | |
|---|---|
| Feed | A mixture of $CH_4$ and $O_2$ |
| $CH_4/O_2$ ratio in feed | 6.0 |
| Space velocity | 10,200 $cm^3 \cdot g^{-1} \cdot h^{-1}$ |
| Temperature | 753° C. |
| Pressure | 1.1 atm |

The results obtained were as follows. The total conversion of methane and the selectivity for ethylene, ethane and $C_{3+4}$ hydrocarbons were 26.8% and 70.6%, respectively. The composition of product stream, after removal of water, was ethylene-5.1%, ethane-3.8%, methane-79.5%, propylene and butenes-0.5%, propane and butanes 0.3%, CO-0.61%, $CO_2$-7.0% and $O_2$-4.0%, etc.

Step-II: Catalytic Conversion of Ethylene and Other Olefins from the Product Stream of Step-I to Liquid Hydrocarbons

| Process conditions employed in Step-II | |
|---|---|
| Temperature | 400° C. |
| Pressure | 14.5 atm |
| GHSV | 600 $h^{-1}$ |

The results obtained were as follows.

| | |
|---|---|
| Total conversion of ethylene | 98.7% |
| Selectivity for liquid hydrocarbons ($C_5$–$C_{10}$ hydrocarbons) | 58.0% |
| Selectivity for $C_3 + C_4$ hydrocarbons (LPG) | 41.9% |

EXAMPLE-6

Conversion of methane to liquid hydrocarbons in the two steps was carried out by the procedures described in EXAMPLE-1 at the following process conditions.

Step-I: Catalytic Oxidative Conversion of Methane to Ethylene, Ethane and $C_{3+4}$ Hydrocarbons The catalyst was the same as that used in EXAMPLE-5.

| Process conditions employed in Step-I | |
|---|---|
| Feed | A mixture of $CH_4$ and $O_2$ |
| $CH_4/O_2$ ratio in feed | 8.0 |
| Space velocity | 20,500 $cm^3 \cdot g^{-1} \cdot h^{-1}$ |
| Temperature | 752° C. |
| Pressure | 1.2 atm. |

The results obtained were as follows. The total conversion of methane and the selectivity for ethylene, ethane and $C_{3+4}$ hydrocarbons were 18.9% and 81.0%, respectively. The composition of product stream after removal of water, was ethylene-3.1%, ethane-4.1%, methane-85.5%, propylene and butenes-0.3%, propane and butanes-0.2%, CO-0.5%, $CO_2$-3.0% and $O_2$-3.5%, etc.

Step-II: Catalytic Conversion of Ethylene and Other Olefins from the Product Stream of Step-I to Liquid Hydrocarbons

| Process conditions employed in Step-II | |
|---|---|
| Temperature | 500° C. |
| Pressure | 14 atm |
| GHSV | 1200 $h^{-1}$ |

The results obtained were as follows.

| Total conversion of ethylene | 94.5% |
|---|---|
| Selectivity for liquid hydrocarbons ($C_5$-$C_{10}$ hydrocarbons) | 79.7% |
| Selectivity for $C_3$ + $C_4$ hydrocarbons (LPG) | 20.1% |

EXAMPLE-7

Conversion of methane to liquid hydrocarbons in the two steps was carried out by the procedures described in EXAMPLE-1 at the following process conditions.

Step-I: Catalytic Oxidative Conversion of Methane to Ethylene, Ethane and $C_{3+4}$ Hydrocarbons The catalyst used was Li-promoted MgO prepared by impregnating magnesium carbonate with lithium acetate (Li/Mg=0.1) and calcining at 750° C. for 6 hours.

| Process conditions employed in Step-I | |
|---|---|
| Feed | A mixture of $CH_4$ and $O_2$ |
| $CH_4/O_2$ ratio in feed | 3.0 |
| GHSV | 10,300 ($cm^3 \cdot g^{-1} \cdot h^{-1}$) |
| Temperature | 752° C. |
| Pressure | 1.05 atm |

The results obtained were as follows. The total conversion of methane and the selectivity for ethylene, ethane and $C_{3+4}$ hydrocarbons were 36.1% and 60.2%, respectively. The composition of product stream after removal of water, was ethylene-6.5%, ethane-3.7%, methane-71.1%, propylene and butenes-0.6%, propane and butanes-0.3%, CO-0.5%, $CO_2$-14.3% and $O_2$-3.3%, etc.

Step-II: Catalytic Conversion of Ethylene and Other Olefins from the Product Stream of Step-I to Liquid Hydrocarbons

| Process conditions employed in Step-II | |
|---|---|
| Temperature | 410° C. |
| Pressure | 7.5 atm |
| GHSV | 1040 $h^{-1}$ |

The results obtained were as follows.

| Total conversion of ethylene | 97.3% |
|---|---|
| Selectivity for liquid hydrocarbons ($C_5$-$C_{10}$ hydrocarbons) | 61.2% |
| Selectivity for $C_3$ + $C_4$ hydrocarbons (LPG) | 35.8% |

EXAMPLE-8

Conversion of methane to liquid hydrocarbons in the two steps was carried out by the procedures described in EXAMPLE-1 at the following process conditions.

Step-I: Catalytic Oxidative Conversion of Methane to Ethylene, Ethane and $C_{3+4}$ Hydrocarbons The catalyst was same as that used in EXAMPLE-7.

| Process conditions employed in Step-I | |
|---|---|
| Feed composition | $CH_4$ 62.3%, $O_2$ 7.7% and $N_2$ 30% |
| $CH_4/O_2$ ratio in feed | 8.1 |
| GHSV | 20,300 ($cm^3 \cdot g^{-1} \cdot h^{-1}$) |
| Temperature | 751° C. |
| Pressure | 1.04 atm |

The results obtained were as follows. The total conversion of methane and the selectivity for ethylene, ethane, and $C_{3+4}$ hydrocarbons were 20.1% and 80.8%, respectively. The composition of product stream after removal of water, was ethylene-2.4%, ethane-2.9%, methane 59.9%, propylene and butenes-0.2%, propane and butane-0.2%, CO-0.25%, $CO_2$-2.7% and balance $O_2$ and $N_2$.

Step-II: Catalytic Conversion of Ethylene and Other Olefins from the Product Stream of Step-I to Liquid Hydrocarbons

| Process conditions employed in Step-II | |
|---|---|
| Temperature | 400° C. |
| Pressure | 14.5 atm |
| GHSV | 1200 $h^{-1}$ |

The results obtained were as follows.

| Total conversion of ethylene | 97.1% |
|---|---|
| Selectivity for liquid hydrocarbons ($C_5$-$C_{10}$ hydrocarbons) | 59.8% |
| Selectivity for $C_3$ + $C_4$ hydrocarbons (LPG) | 32.2% |

EXAMPLE-9

Conversion of methane to liquid hydrocarbons in the two steps was carried out by the procedures described in EXAMPLE-1 at the following process conditions.

Step-I: Catalytic Oxidative Conversion of Methane to Ethylene, Ethane and $C_{3+4}$ Hydrocarbons The catalyst used was PbO-MgO prepared by impregnating magnesium hydroxide with lead nitrate (Pb/Mg=0.02) and calcining at 900° C. for 5 hours.

| Process conditions employed in Step-I | |
|---|---|
| Feed composition | $CH_4$ 20%, $O_2$ 5% and $H_2O$ 75% |
| $CH_4/O_2$ ratio in feed | 4.0 |
| GHSV | 10,600 ($cm^3 \cdot g^{-1} \cdot h^{-1}$) |
| Temperature | 850° C. |
| Pressure | 1.1 atm |

The results obtained were as follows. The total conversion of methane and the selectivity for ethylene, ethane and $C_{3+4}$ hydrocarbons were 29.1% and 68.0%, respectively. The composition of product stream after removal of water was ethylene-7.4%, ethane-3.2%, methane-78.5%, propylene and butanes-0.2%, propane and butanes-0.1%, CO-0.1%, $CO_2$-9.7% and $O_2$-0.8%, etc.

Step-II: Catalytic Conversion of Ethylene and Other Olefins from the Product Stream of Step-I to Liquid Hydrocarbons

| Process conditions employed in Step-II | |
|---|---|
| Temperature | 500° C. |
| Pressure | 15.0 atm |
| GHSV | 1050 $h^{-1}$ |

The results obtained were as follows.

| | |
|---|---|
| Total conversion of ethylene | 99.2% |
| Selectivity for liquid hydrocarbons ($C_5$-$C_{10}$ hydrocarbons) | 68.9% |
| Selectivity for $C_3$ + $C_4$ hydrocarbons (LPG) | 30.6% |

EXAMPLE-10

The conversion of methane into liquid hydrocarbons in the two steps was carried out by the procedures described in EXAMPLE-1 except that the gaseous products after removal of the liquid hydrocarbons by condensation, were recycled back to the reactor of Step-I.

Step-I: Catalytic Oxidative Conversion of Methane to Ethylene, Ethane and $C_{3+4}$ Hydrocarbons The catalyst was same as that used in EXAMPLE-9.

| Process conditions employed in Step-I | |
|---|---|
| Temperature | 802° C. |
| Pressure | 1.07 atm |
| Hydrocarbon/steam ratio | 0.25 |
| Hydrocarbon/$O_2$ ratio | 5.0 |
| Total space velocity | 10,500 ($cm^3 \cdot g^{-1} \cdot h^{-1}$) |
| Space velocity of recycled gas | 8,700 ($cm^3 \cdot g^{-1} \cdot h^{-1}$) |

The composition of product stream, after removal of water, was ethylene 5.1%, ethane 4.9%, propylene and butenes 0.3%, propane and butanes 0.2%, and balance methane, CO, $CO_2$ and $O_2$.

Step-II: Catalytic Conversion of Ethylene and Other Olefins from the Product Stream of Step-I to Liquid Hydrocarbons

| Process conditions employed in Step-II | |
|---|---|
| Temperature | 450° C. |
| Pressure | 2.0 atm |
| GHSV | 500 $h^{-1}$ |

The results obtained were as follows. Total conversion of ethylene, selectivity for liquid hydrocarbons and for $C_3+C_4$ (LPG) hydrocarbons were 76.8%, 28.2% and 49.8%, respectively. The distribution of $C_5$-$C_8$ paraffins, $C_6$-$C_8$ aromatics and $C_9$-$C_{10}$ hydrocarbons in the liquid hydrocarbons was 29.2, 69.9, and 0.9 wt %, respectively. The gaseous product after removal of liquid hydrocarbons (i.e. $C_5$-$C_{10}$ hydrocarbons) by condensation, were recycled to the reactor of Step-I.

The main novel features and advantages of the invention are as follows:

(i) By the present two-step process, the conversion of methane into liquid hydrocarbons of gasoline range could be achieved in an energy efficient manner as there is no involvement of the methane-to-syngas conversion step.

(ii) The product stream obtained from the first-step of the present process, after removing water by condensation, is used directly as a feed for the second step, thus avoiding the high cost separation of ethylene and other olefins existing at low concentrations in the product stream of the first step. The liquid hydrocarbons formed in the second step of the present process could be separated from the product stream with ease.

(iii) The feed raw materials required in the present process are only methane, oxygen (or air) and steam.

(iv) There are no problems of corrosion in the process.

(v) The selectivity and yield for $C_2$-hydrocarbons in the first step and for liquid hydrocarbons of gasoline range in the second step of the present process are high.

(vi) The distribution of hydrocarbons formed in the second step viz. liquified petroleum gas ($C_3$ and $C_4$ hydrocarbons) and gasoline range liquid hydrocarbons comprising $C_5$-$C_8$ paraffins, $C_6$-$C_8$ aromatics and $C_{9+}$ hydrocarbons could be controlled by changing process conditions of the second step.

We claim:

1. An improved integrated two-step process for the conversion of methane to liquid hydrocarbons of gasoline range which comprises (i) passing continuously a gaseous mixture comprising methane and oxygen over a basic solid rare earth metal promoted alkaline earth metal oxide catalyst suitable for oxidative coupling of methane to $C_2$ hydrocarbons in a fixed bed reactor at a pressure in the range of 1–50 atmospheres, a temperature in the range of 500°–1000° C., a $CH_4/O_2$ ratio in the feed in the range of 1.5–100, and a gas hourly space velocity in the range of 500–5,000,000 $h^{-1}$ and separating the water from the product stream by known methods, and (ii) passing continuously the gaseous product stream of step (i) over a solid acid catalyst containing high silica pentasil zeolite having a channel diameter of 5–6 Å in a fixed bed reactor at a pressure in the range of 1–50 atmospheres, a temperature in the range of 200°–700° C. and at a gas hourly space velocity in the range of 100–50,000 $h^{-1}$, separating the liquid hydrocarbons and oxides of carbon by known methods and recycling the $C_1$–$C_2$ hydrocarbons and unconverted oxygen to step (i).

2. An improved integrated two-step process as claimed in claim 1 wherein the pressure employed in the first step ranges from about 1 to 2 atm.

3. An improved integrated two step process as claimed in claim 1 wherein the temperature in step (i) ranges from about 600°–850° C.

4. An improved integrated two step process as claimed in claim 1 wherein the methane/$O_2$ ratio in the feed for step (i) ranges from 2 to 20.

5. An improved integrated two-step process as claimed in claim 1 wherein the concentration of methane in the feed for step (i) ranges from 20–95 mol %.

6. An improved integrated two-step process as claimed in claim 1 wherein the concentration of $O_2$ in the feed for step (i) ranges from 1–33 mol. %.

7. An improved integrated two-step process as claimed in claim 1 wherein the concentration of $N_2$, in the feed for step (i) ranges from 0–80 mol. %.

8. An improved integrated two-step process as claimed in claim 1 wherein the concentration of $CO_2$ in the feed for step (i) ranges from 0–30 mol %.

9. An improved integrated two-step process as claimed in claim 1 wherein the concentration of ethane in the feed for step (i) ranges from 0–5 mol %.

10. An improved integrated two-step process as claimed in claim 1 wherein the gas hourly space velocity in step (i) ranges from 2,000 to 2,000,000 $h^{-1}$.

11. An improved integrated two step process as claimed in claim 1 wherein the pressure employed in step (ii) ranges from 2 to 30 atm.

12. An improved integrated two-step process as claimed in claim 1 wherein the temperature in step (ii) ranges from 300° to 600° C.

13. An improved integrated two-step process as claimed in claim 1 wherein the gas hourly space velocity in step (ii) ranges from 200 to 20,000 $h^{-1}$.

14. An improved integrated two step process as claimed in claim 1 wherein the solid acid catalyst is selected from the group consisting of H-ZSM-5, H-ZSM-8, H-ZSM-11 and Pt-H-ZSM-5.$Al_2O_3$.

15. An improved integrated two step process as claimed in claim 1 wherein the basic solid rare earth promoted alkaline earth metal oxide catalyst is selected from the group consisting of $La_2O_3$-MgO, $La_2O_3$-CaO and $Sm_2O_3$-MgO.

* * * * *